United States Patent
Farhi et al.

(10) Patent No.: US 12,048,758 B2
(45) Date of Patent: Jul. 30, 2024

(54) PRESERVING AGENT COMPRISING 4-(3-ETHOXY-4-HYDROXYPHENYL)-2-BUTANONE, AND USE THEREOF IN COSMETIC COMPOSITIONS

(71) Applicant: L'OREAL, Paris (FR)

(72) Inventors: Gaelle Farhi, Saint Ouen (FR); Gaelle Moneuze, Chevilly-Larue (FR); Damien Drillon, Saint Ouen (FR); Julien Galvan, Chevilly-Larue (FR)

(73) Assignee: L'OREAL, Paris (FR)

( * ) Notice: Subject to any disclaimer, the term of this patent is extended or adjusted under 35 U.S.C. 154(b) by 43 days.

(21) Appl. No.: 16/471,658

(22) PCT Filed: Dec. 20, 2017

(86) PCT No.: PCT/EP2017/083708
§ 371 (c)(1),
(2) Date: Jun. 20, 2019

(87) PCT Pub. No.: WO2018/115058
PCT Pub. Date: Jun. 28, 2018

(65) Prior Publication Data
US 2021/0275417 A1  Sep. 9, 2021

(30) Foreign Application Priority Data
Dec. 22, 2016 (FR) ...................................... 1663102

(51) Int. Cl.
| | | |
|---|---|---|
| *A61K 8/35* | (2006.01) | |
| *A61K 8/34* | (2006.01) | |
| *A61K 8/368* | (2006.01) | |
| *A61K 8/41* | (2006.01) | |
| *A61K 8/49* | (2006.01) | |
| *A61K 8/898* | (2006.01) | |
| *A61Q 5/12* | (2006.01) | |

(52) U.S. Cl.
CPC ................ *A61K 8/35* (2013.01); *A61K 8/342* (2013.01); *A61K 8/345* (2013.01); *A61K 8/368* (2013.01); *A61K 8/416* (2013.01); *A61K 8/4946* (2013.01); *A61K 8/898* (2013.01); *A61Q 5/12* (2013.01); *A61K 2800/524* (2013.01)

(58) Field of Classification Search
CPC .. A61K 8/368; A61K 8/898; A61K 2800/524; A61K 8/35; A61K 8/345; A61K 8/342; A61K 8/416; A61K 8/4946; A61Q 5/12
See application file for complete search history.

(56) References Cited

U.S. PATENT DOCUMENTS

| | | | |
|---|---|---|---|
| 7,601,340 B2 * | 10/2009 | Nojiri | A61K 8/4973 424/70.28 |
| 2007/0231354 A1 * | 10/2007 | Sogabe | C08F 220/585 424/401 |
| 2009/0232756 A1 | 9/2009 | Monello | |
| 2014/0057997 A1 * | 2/2014 | Chevalier | A61K 8/37 514/772 |
| 2016/0220475 A1 * | 8/2016 | Scherner | A61K 8/345 |

FOREIGN PATENT DOCUMENTS

WO  WO-2011042358 A1 *  4/2011  ............. A61Q 17/04

* cited by examiner

*Primary Examiner* — Jianfeng Song
(74) *Attorney, Agent, or Firm* — POLSINELLI PC

(57) ABSTRACT

The present invention relates to a preserving agent for a cosmetic composition, comprising 4-(3-ethoxy-4-hydroxyphenyl)-2-butanone and a second compound chosen from salicylic acid, the compounds of formula (II), salts thereof, esters thereof with an alcohol containing from 1 to 4 carbon atoms, and a mixture of these compounds. The present invention also relates to the use of the preserving agent for preserving cosmetic compositions. The present invention also relates to a cosmetic composition comprising the above preserving agent. Finally, the present invention relates to the use of the cosmetic composition for treating keratin fibres, preferably human keratin fibres such as the hair.

7 Claims, No Drawings

PRESERVING AGENT COMPRISING 4-(3-ETHOXY-4-HYDROXYPHENYL)-2-BUTANONE, AND USE THEREOF IN COSMETIC COMPOSITIONS

CROSS REFERENCE TO RELATED APPLICATIONS

This application is a National Phase filing under 35 U.S.C. § 371 of PCT/EP2017/083708 filed on Dec. 20, 2017; which application in turn claims priority to Application No. 1663102 filed in France on Dec. 22, 2016. The entire contents of each application are hereby incorporated by reference.

The present invention relates to a preserving agent for a cosmetic composition comprising a combination of 4-(3-ethoxy-4-hydroxyphenyl)-2-butanone and of a second compound chosen from salicylic acid, the acids of formula (II) below, salts thereof, esters thereof with an alcohol containing from 1 to 4 carbon atoms, and a mixture of these compounds:

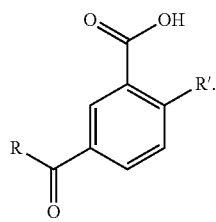

(II)

The present invention also relates to the use of this agent for preserving cosmetic compositions, preferably for protecting cosmetic compositions against bacterial contamination.

The invention also relates to a cosmetic composition comprising this preserving agent.

Finally, the invention relates to the use of such a cosmetic composition for treating keratin fibres, preferably human keratin fibres such as the hair.

It is common practice to introduce chemical preserving agents into cosmetic compositions such as those intended especially for hair treatment, these preserving agents being intended to combat the growth of microorganisms in these compositions, which would rapidly make them unsuitable for use.

It is in particular necessary to protect compositions against microorganisms that are capable of growing inside the composition, for example during their manufacture, and also against those which the user might introduce therein while handling it, in particular when taking up products in a jar with the fingers.

Chemical preserving agents commonly used are in particular parabens, organic acids or formaldehyde-releasing compounds.

However, these preserving agents have the drawback of occasionally causing irritation, in particular on sensitive skin, especially when they are present at relatively high levels.

Moreover, these preserving agents must not modify the texture, the colour or the odour of the compositions in which they are contained.

Finally, in the interests of the environment, consumers are increasingly in search of environmentally friendly, in particular non-ecotoxic, preserving agents.

WO 2011/039445 discloses preserving agents based on vanillin derivatives, for instance the compound 4-(3-ethoxy-4-hydroxyphenyl)-2-butanone.

However, in order to have efficient protection equivalent to that of the prior art, this compound alone must be used in high contents, which has the effect of increasing the cost of the composition.

Consequently, there is a need to develop a novel preserving agent that can address the drawbacks of the prior art.

It has now been found, entirely surprisingly, that a combination of 4-(3-ethoxy-4-hydroxyphenyl)-2-butanone and of a second compound such as salicylic acid or a derivative thereof, makes it possible to obtain a synergistic preserving effect, which makes it possible in particular to use smaller amounts of preserving agents while at the same time maintaining very good preserving efficacy.

Thus, a first subject of the invention is a preserving agent for a cosmetic composition comprising:
a first compound of formula (I) below:

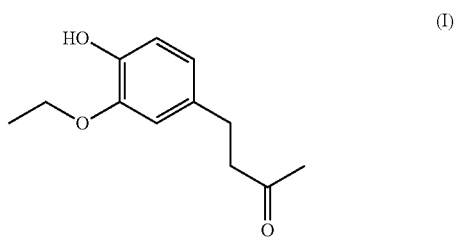

(I)

a second compound chosen from salicylic acid, the acids of formula (II) below, salts thereof, esters thereof with an alcohol containing from 1 to 4 carbon atoms, and a mixture of these compounds:

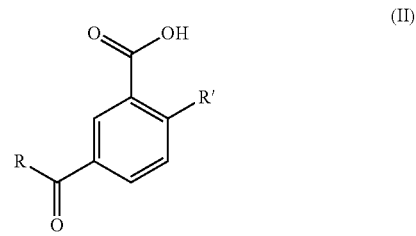

(II)

in which formula:
the radical R is chosen from the following groups: a linear or branched, cyclic or non-cyclic, saturated aliphatic chain, containing from 2 to 22 carbon atoms; an unsaturated chain containing from 2 to 22 carbon atoms, containing one or more conjugated or non-conjugated double bonds; an aromatic nucleus bonded to the carbonyl radical directly or via saturated or unsaturated aliphatic chains containing from 2 to 7 carbon atoms; said groups possibly being substituted with one or more substituents, which may be identical or different, chosen from (a) halogen atoms, (b) the trifluoromethyl group, (c) hydroxyl groups in free form or esterified with an acid containing from 1 to 6 carbon atoms, and (d) a carboxyl function in free form or esterified with a lower alcohol containing from 1 to 6 carbon atoms;
the radical R' denotes a hydroxyl group.

The preserving agent according to the invention makes it possible to protect cosmetic compositions against contamination by microorganisms without, however, "overprotecting" them, which considerably limits the risk of sensitization of consumers.

Consequently, the 4-(3-ethoxy-4-hydroxyphenyl)-2-butanone in the preserving agent according to the invention may be used in lower proportions than in the prior art.

The preserving agent according to the invention does not impair the texture, colour or odour of the cosmetic compositions into which it is incorporated.

It also has a good environmental profile, unlike standard preserving agents, which allows the preparation of cosmetic compositions that have less of an environmental impact.

A subject of the invention is also the use of the preserving agent for preserving cosmetic compositions, preferably for protecting cosmetic compositions against contamination with microorganisms and in particular against bacterial contamination.

Another subject of the present invention is a cosmetic composition comprising an aqueous support and the preserving agent.

The use of the preserving agent according to the invention is particularly advantageous in cosmetic hair compositions, i.e. compositions for treating human keratin fibres.

Finally, a subject of the present invention is the use of this cosmetic composition for treating keratin fibres, preferably human keratin fibres such as the hair.

Other subjects, characteristics, aspects and advantages of the invention will emerge even more clearly on reading the description and the examples that follow.

In the text hereinbelow, and unless otherwise indicated, the limits of a range of values are included within that range, especially in the expressions "between" and "ranging from . . . to . . . ".

Moreover, the expressions "at least one" and "at least" used in the present description are equivalent to the expressions "one or more" and "greater than or equal to", respectively.

According to the present patent application, the term "keratin fibres" mainly denotes human keratin fibres and in particular the hair.

As explained previously, the preserving agent according to the invention comprises a first compound of formula (I) below:

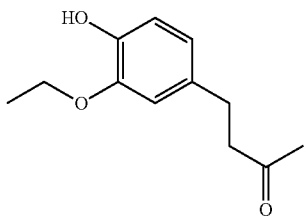

This compound is named 4-(3-ethoxy-4-hydroxyphenyl)-2-butanone and is described especially in patent application WO 2011/039445.

The preserving agent according to the invention comprises a second compound chosen from:
  salicylic acid,
  the acids of formula (II) below,
  salts of salicylic acid and of the acids of formula (II),
  esters of salicylic acid and of the acids of formula (II) with an alcohol containing from 1 to 4 carbon atoms,
  and a mixture of these compounds.

Formula (II) of the acids that may be used is as follows:

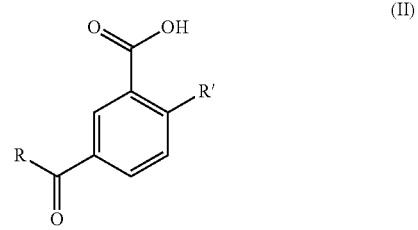

in which formula:
  the radical R is chosen from the following groups: a linear or branched, cyclic or non-cyclic, saturated aliphatic chain, containing from 2 to 22 carbon atoms; an unsaturated chain containing from 2 to 22 carbon atoms, containing one or more conjugated or non-conjugated double bonds; an aromatic nucleus bonded to the carbonyl radical directly or via saturated or unsaturated aliphatic chains containing from 2 to 7 carbon atoms;
  said groups possibly being substituted with one or more substituents, which may be identical or different, chosen from (a) halogen atoms, (b) the trifluoromethyl group, (c) hydroxyl groups in free form or esterified with an acid containing from 1 to 6 carbon atoms, and (d) a carboxyl function in free form or esterified with a lower alcohol containing from 1 to 6 carbon atoms;
  the radical R' denotes a hydroxyl group.

The term "esters of salicylic acid with an alcohol containing from 1 to 4 carbon atoms" means the compounds of formula (III) below:

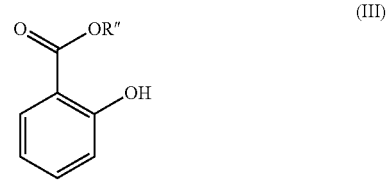

in which formula (III) R" denotes an alkyl radical comprising from 1 to 4 carbon atoms.

The term "esters of an acid of formula (II) with an alcohol containing from 1 to 4 carbon atoms" means the compounds of formula (IV)_below:

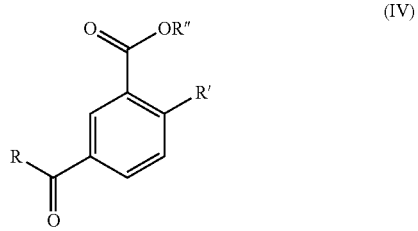

in which formula (IV) R and R' are as defined above and R" denotes an alkyl radical comprising from 1 to 4 carbon atoms.

Preference is given to alcohol esters containing 1 or 2 carbon atoms, i.e. those of formulae (III) and (IV) above in which R" denotes an alkyl radical comprising 1 or 2 carbon atoms.

The term "salts of salicylic acid or of the acids of formula (II)" means any compound in which salicylic acid or the acid of formula (II) is in anionic form, combined with any mineral or organic cation. Use is preferably made of salts derived from a mineral or organic base.

Examples of mineral bases that may especially be mentioned include alkali metal or alkaline-earth metal hydroxides, for instance sodium hydroxide or potassium hydroxide, or aqueous ammonia.

Organic bases that may especially be mentioned include amines and alkanolamines.

Preferably, in formulae (II) and (IV), the radical R is chosen from the following groups: a linear or branched, cyclic or non-cyclic, saturated aliphatic chain containing from 3 to 11 carbon atoms; an unsaturated chain containing from 7 to 17 carbon atoms, containing one or more conjugated or non-conjugated double bonds;

said groups possibly being substituted with one or more substituents, which may be identical or different, chosen from (a) halogen atoms, (b) the trifluoromethyl group, (c) hydroxyl groups in free form or esterified with an acid containing from 1 to 6 carbon atoms, and (d) a carboxyl function in free form or esterified with a lower alcohol containing from 1 to 6 carbon atoms.

More preferably, the radical R is a linear or branched, cyclic or non-cyclic, saturated aliphatic chain containing from 3 to 11 carbon atoms.

Preferably, the second compound of the preserving agent according to the invention is chosen from salicylic acid, the acids of formula (II), and salts thereof.

The second compound of the preserving agent according to the invention is more particularly chosen from salicylic acid, 5-n-decanoylsalicylic acid, 5-n-dodecanoylsalicylic acid, 5-n-heptyloxysalicylic acid, salts thereof, and a mixture of these compounds.

More preferentially, the second compound is chosen from salicylic acid, salts thereof and a mixture of these compounds.

Better still, the second compound is chosen from salicylic acid and salts thereof.

The weight ratio of the first compound to the second compound generally ranges from 0.01 to 10, preferably from 0.1 to 5, more preferentially from 0.2 to 2.

In one particular variant of the invention, the preserving agent also comprises one or more diols comprising from 2 to 6 carbon atoms, preferably from 2 to 4 carbon atoms and in particular 3 carbon atoms.

In this variant, the diol(s) that may be used in the preserving agent according to the invention are preferably chosen from 1,2-propanediol, 1,3-propanediol, and a mixture of these compounds, and, more preferentially, the diol is 1,3-propanediol.

In this particular variant of the invention, the weight ratio of the first compound to the diol(s) generally ranges from 0.01 to 1 and preferably from 0.05 to 0.5.

The preserving agent as defined above allows the conservation of cosmetic compositions, preferably for protecting cosmetic compositions against contamination with microorganisms.

In particular, the contamination may be due to fungi such as *Aspergillus niger*, yeasts such as *Candida albicans* or bacteria such as *Enterococcus faecalis, Escherichia coli, Staphylococcus aureus* and *Pseudomonas aeruginosa*.

Consequently, another subject of the invention is the use of the preserving agent as defined above for preserving cosmetic compositions, preferably for protecting cosmetic compositions against contamination with microorganisms and in particular against bacterial contamination.

A subject of the invention is also a cosmetic composition comprising an aqueous support and a preserving agent as defined above.

The term "aqueous support" means a medium comprising water or a mixture of water and one or more organic solvents.

Water generally represents from 30% to 98% by weight, preferably from 50% to 95% by weight and more preferentially from 60% to 92% by weight relative to the total weight of the composition.

Preferably, the organic solvent(s) are chosen from hydrophilic organic solvents, more preferentially chosen from linear or branched monoalcohols containing from 1 to 8 carbon atoms, and mixtures of these compounds.

Preferably, the organic solvent(s) are chosen from ethanol, propanol, butanol, isopropanol, isobutanol, and mixtures of these compounds.

The organic solvent(s) generally represent from 1% to 15% by weight and preferably from 5% to 10% by weight relative to the total weight of the composition.

Preferably, the aqueous support of the composition according to the invention is water.

Preferably, the first compound of formula (I) is present in a content of from 0.0001% to 5% by weight, preferably from 0.001% to 1% by weight, more preferentially from 0.005% to 0.5% by weight and in particular from 0.005% to 0.1% by weight relative to the total weight of the composition.

Preferably, the second compound is present in a content of from 0.001% to 1% by weight, more preferentially from 0.005% to 0.5% by weight and in particular from 0.01% to 0.05% by weight relative to the total weight of the composition.

In a preferred variant of the invention, the composition comprises one or more diols as defined previously.

When they are present, the diol(s) are generally in a total content ranging from 0.001% to 5% by weight, preferably from 0.01% to 1% by weight and more preferentially from 0.05% to 0.5% by weight, relative to the total weight of the composition.

The composition according to the invention may also comprise one or more surfactants, more particularly nonionic, anionic, cationic, or amphoteric or zwitterionic surfactants.

The nonionic surfactant(s) that may be used in the composition according to the invention are described, for example, in the Handbook of Surfactants by M. R. Porter, published by Blackie & Son (Glasgow and London), 1991, pages 116-178. They are chosen especially from alcohols, α-diols and (C1-C20)alkylphenols, these compounds being polyethoxylated, polypropoxylated and/or polyglycerolated, and containing at least one fatty chain comprising, for example, from 8 to 18 carbon atoms, it being possible for the number of ethylene oxide and/or propylene oxide groups to especially range from 2 to 50, and for the number of glycerol groups to especially range from 2 to 30.

Mention may also be made of copolymers of ethylene oxide and propylene oxide, polyoxyalkylenated fatty acid esters, optionally oxyalkylenated alkylpolyglycosides, alkyl glucoside esters, N-alkylglucamine and N-acyl-methylglucamine derivatives, aldobionamides and amine oxides.

Unless otherwise mentioned, for these surfactants the term "fatty" compound (for example a fatty acid) denotes a compound comprising, in its main chain, at least one saturated or unsaturated alkyl chain comprising at least 6 carbon atoms, preferably from 8 to 30 carbon atoms, and better still from 10 to 22 carbon atoms.

The term "anionic surfactant" means a surfactant comprising, as ionic or ionizable groups, only anionic groups. These anionic groups are preferably chosen from the groups $CO_2H$, $CO_2^-$, $SO_3H$, $SO_3^-$, $OSO_3H$, $OSO_3^-$, $O_2PO_2H$, $O_2PO_2H^-$ and $O_2PO_2^{2-}$.

The anionic surfactant(s) that may be used in the composition of the invention are chosen in particular from alkyl sulfates, alkyl ether sulfates, alkylamido ether sulfates, alkylaryl polyether sulfates, monoglyceride sulfates, alkylsulfonates, alkylamide sulfonates, alkylarylsulfonates, α-olefin sulfonates, paraffin sulfonates, alkylsulfosuccinates, alkyl ether sulfosuccinates, alkylamide sulfosuccinates, alkyl sulfoacetates, acylsarcosinates, acylglutamates, alkylsulfosuccinamates, acylisethionates and N-acyltaurates, salts of alkyl monoesters and polyglycoside-polycarboxylic acids, acyllactylates, salts of D-galactoside uronic acids, salts of alkyl ether carboxylic acids, salts of alkyl aryl ether carboxylic acids, and salts of alkylamido ether carboxylic acids; or the non-salified forms of all of these compounds, the alkyl and acyl groups of all of these compounds comprising from 6 to 24 carbon atoms and the aryl group denoting a phenyl group.

Some of these compounds may be oxyethylenated and then preferably comprise from 1 to 50 ethylene oxide units.

The salts of $C_6$-$C_{24}$ alkyl monoesters and of polyglycoside-polycarboxylic acids may be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates.

When the anionic surfactant(s) are in salt form, they are not in the form of zinc salts, and they may be chosen from alkali metal salts, such as the sodium or potassium salt, and preferably the sodium salt, ammonium salts, amine salts, and in particular amino alcohol salts, and alkaline-earth metal salts such as the magnesium salt.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts and in particular the sodium or magnesium salts are preferably used.

Use is preferably made of $(C_6$-$C_{24})$alkyl sulfates, $(C_6$-$C_{24})$alkyl ether sulfates, which are optionally oxyethylenated, comprising from 2 to 50 ethylene oxide units, and mixtures thereof, in particular in the form of alkali metal salts or alkaline-earth metal salts, ammonium salts or amino alcohol salts. More preferentially, the anionic surfactant(s) are chosen from $(C_{10}$-$C_{20})$alkyl ether sulfates, and in particular sodium lauryl ether sulfate containing 2.2 mol of ethylene oxide.

Preferably, the composition according to the invention comprises one or more cationic surfactants.

The term "cationic surfactant" means a surfactant that is positively charged when it is contained in the composition according to the invention. This surfactant may bear one or more positive permanent charges or may contain one or more cationizable functions within the composition according to the invention.

The cationic surfactant(s) are preferably chosen from primary, secondary or tertiary fatty amines, which are optionally polyoxyalkylenated, or salts thereof, and quaternary ammonium salts, and mixtures thereof.

The fatty amines generally comprise at least one $C_8$-$C_{30}$ hydrocarbon-based chain.

Examples of quaternary ammonium salts that may especially be mentioned include:

those corresponding to the general formula (V) below:

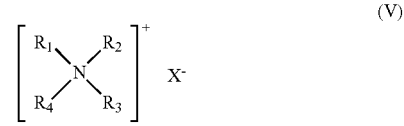

in which the groups $R_1$ to $R_4$, which may be identical or different, represent a linear or branched aliphatic group comprising from 1 to 30 carbon atoms, or an aromatic group such as aryl or alkylaryl, at least one of the groups $R_1$ to $R_4$ denoting a linear or branched aliphatic radical comprising from 8 to 30 carbon atoms, preferably from 12 to 24 carbon atoms. The aliphatic groups may comprise heteroatoms especially such as oxygen, nitrogen, sulfur and halogens. The aliphatic groups are chosen, for example, from $C_1$-$C_{30}$ alkyl, $C_1$-$C_{30}$ alkoxy, polyoxy$(C_2$-$C_6)$alkylene, $C_1$-$C_{30}$ alkylamide, $(C_{12}$-$C_{22})$alkylamido$(C_2$-$C_6)$alkyl, $(C_{12}$-$C_{22})$alkyl acetate and $C_1$-$C_{30}$ hydroxyalkyl groups; $X^-$ is an anion chosen from the group of the halides, phosphates, acetates, lactates, $(C_1$-$C_4)$alkyl sulfates, $(C_1$-$C_4)$alkylsulfonates and $(C_1$-$C_4)$alkylarylsulfonates.

Among the quaternary ammonium salts of formula (V), the ones that are preferred are, on the one hand, tetraalkylammonium salts, for instance dialkyldimethylammonium or alkyltrimethylammonium salts in which the alkyl group comprises approximately from 12 to 22 carbon atoms, in particular behenyltrimethylammonium, distearyldimethylammonium, cetyltrimethylammonium or benzyldimethylstearylammonium salts, or, on the other hand, the palmitylamidopropyltrimethylammonium salt, the stearamidopropyltrimethylammonium salts, the stearamidopropyldimethylcetearylammonium salts, or the stearamidopropyldimethyl(myristyl acetate)ammonium salts sold under the name Ceraphyl® 70 by the company Van Dyk. It is preferred in particular to use the chloride salts of these compounds;

quaternary ammonium salts of imidazoline, for instance those of formula (VI) below:

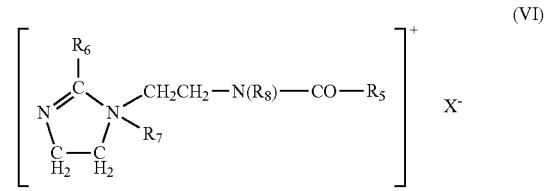

in which $R_5$ represents an alkenyl or alkyl group comprising from 8 to 30 carbon atoms, for example tallow fatty acid derivatives, $R_6$ represents a hydrogen atom, a $C_1$-$C_4$ alkyl group or an alkenyl or alkyl group comprising from 8 to 30 carbon atoms, $R_7$ represents a $C_1$-$C_4$ alkyl group, $R_8$ represents a hydrogen atom or a $C_1$-$C_4$ alkyl group and $X^-$ is an anion chosen from the group of the halides, phosphates, acetates, lactates, alkyl sulfates, alkylsulfonates or alkylarylsulfonates, the alkyl and aryl groups of which preferably comprise, respectively, from 1 to 20 carbon atoms and from 6 to 30 carbon atoms. Preferably, $R_5$ and $R_6$ denote a mixture of alkenyl or alkyl groups comprising from 12 to 21 carbon atoms, for example derived from tallow fatty acids, $R_7$ denotes a methyl group and $R_8$ denotes a hydrogen atom. Such a product is sold, for example, under the name Rewoquat® W 75 by the company Rewo;

diquaternary or triquaternary ammonium salts, in particular of formula (VII):

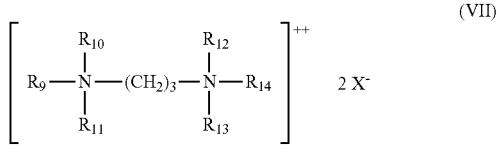

in which $R_9$ denotes an alkyl radical comprising approximately from 16 to 30 carbon atoms, which is optionally hydroxylated and/or interrupted with one or more oxygen atoms, $R_{10}$ is chosen from hydrogen and an alkyl radical comprising from 1 to 4 carbon atoms and a group $(R_{9a})(R_{10a})(R_{11a})N—(CH_2)_3$, $R_{9a}$, $R_{10a}$, $R_{11a}$, $R_{11}$, $R_{12}$, $R_{13}$ and $R_{14}$, which may be identical or different, are chosen from hydrogen and an alkyl radical comprising from 1 to 4 carbon atoms, and $X^-$ is an anion chosen from the group of halides, acetates, phosphates, nitrates and methyl sulfates. Such compounds are, for example, Finquat CT-P, sold by the company Finetex (Quaternium 89), and Finquat CT, sold by the company Finetex (Quaternium 75);

quaternary ammonium salts containing at least one ester function, such as those of formula (VIII) below:

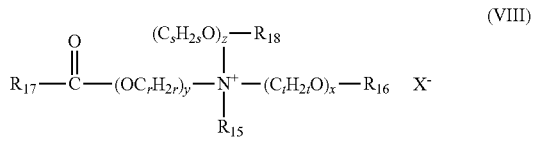

in which:
$R_{15}$ is chosen from $C_1$-$C_6$ alkyl groups and $C_1$-$C_6$ hydroxyalkyl or dihydroxyalkyl groups;
$R_{16}$ is chosen from:
the group

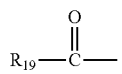

groups $R_{20}$, which are linear or branched, saturated or unsaturated $C_1$-$C_{22}$ hydrocarbon-based groups,
a hydrogen atom,
$R_{18}$ is chosen from:
the group

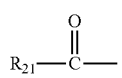

groups $R_{22}$, which are linear or branched, saturated or unsaturated $C_1$-$C_6$ hydrocarbon-based groups,
a hydrogen atom,
$R_{17}$, $R_{19}$ and $R_{21}$, which may be identical or different, are chosen from linear or branched, saturated or unsaturated $C_7$-$C_{21}$ hydrocarbon-based groups;

r, s and t, which may be identical or different, are integers ranging from 2 to 6;
y is an integer ranging from 1 to 10;
x and z, which may be identical or different, are integers ranging from 0 to 10;
$X^-$ is a simple or complex and organic or mineral anion;
with the proviso that the sum x+y+z is from 1 to 15, that when x is 0 then $R_{16}$ denotes $R_{20}$, and that when z is 0 then $R_{18}$ denotes $R_{22}$.

The alkyl groups $R_{15}$ may be linear or branched, and more particularly linear.

Preferably, $R_{15}$ denotes a methyl, ethyl, hydroxyethyl or dihydroxypropyl group, and more particularly a methyl or ethyl group.

Advantageously, the sum x+y+z is from 1 to 10.

When $R_{16}$ is a hydrocarbon-based group $R_{20}$, it may be long and contain from 12 to 22 carbon atoms, or may be short and contain from 1 to 3 carbon atoms.

When $R_{18}$ is a hydrocarbon-based group $R_{22}$, it preferably contains 1 to 3 carbon atoms.

Advantageously, $R_{17}$, $R_{19}$ and $R_{21}$, which may be identical or different, are chosen from linear or branched, saturated or unsaturated $C_{11}$-$C_{21}$ hydrocarbon-based groups, and more particularly from linear or branched, saturated or unsaturated $C_{11}$-$C_{21}$ alkyl and alkenyl groups.

Preferably, x and z, which may be identical or different, are equal to 0 or 1.

Advantageously, y is equal to 1.

Preferably, r, s and t, which may be identical or different, are equal to 2 or 3, and even more particularly are equal to 2.

The anion $X^-$ is preferably a halide (chloride, bromide or iodide) or an alkyl sulfate, more particularly methyl sulfate. However, use may be made of methanesulfonate, phosphate, nitrate, tosylate, an anion derived from an organic acid, such as acetate or lactate, or any other anion that is compatible with the ammonium bearing an ester function.

The anion $X^-$ is even more particularly chloride or methyl sulfate.

Use is made more particularly, in the composition that may be used in the process according to the invention, of the ammonium salts of formula (VIII) in which:
$R_{15}$ denotes a methyl or ethyl group,
x and y are equal to 1;
z is equal to 0 or 1;
r, s and t are equal to 2;
$R_{16}$ is chosen from:
the group

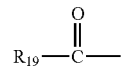

methyl, ethyl or $C_{14}$-$C_{22}$ hydrocarbon-based groups,
a hydrogen atom;
$R_{18}$ is chosen from:
the group

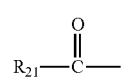

a hydrogen atom;
$R_{17}$, $R_{19}$ and $R_{21}$, which may be identical or different, are chosen from linear or branched, saturated or unsaturated $C_{13}$-$C_{17}$ hydrocarbon-based groups, and preferably from linear or branched, saturated or unsaturated $C_{13}$-$C_{17}$ alkyl and alkenyl groups.

Advantageously, the hydrocarbon-based groups are linear.

Examples that may be mentioned include the compounds of formula (VIII) such as the diacyloxyethyldimethylammonium, diacyloxyethylhydroxyethylmethylammonium, monoacyloxyethyldihydroxyethylmethylammonium, triacyloxyethylmethylammonium and monoacyloxyethylhydroxyethyldimethylammonium salts (chloride or methyl sulfate in particular), and mixtures thereof. The acyl groups preferably contain 14 to 18 carbon atoms and are derived more particularly from a plant oil such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with $C_{10}$-$C_{30}$ fatty acids or with mixtures of $C_{10}$-$C_{30}$ fatty acids of plant or animal origin, or by transesterification of the methyl esters thereof. This esterification is followed by a quaternization using an alkylating agent such as an alkyl halide (preferably a methyl or ethyl halide), a dialkyl sulfate (preferably a methyl or ethyl sulfate), methyl methanesulfonate, methyl para-toluenesulfonate, glycol chlorohydrin or glycerol chlorohydrin.

Such compounds are sold, for example, under the names Dehyquart® by the company Henkel, Stepanquat® by the company Stepan, Noxamium® by the company CECA or Rewoquat® WE 18 by the company Rewo-Witco.

The composition according to the invention may contain, for example, a mixture of quaternary ammonium monoester, diester and triester salts with a weight majority of diester salts.

Use may also be made of the ammonium salts containing at least one ester function that are described in patents U.S. Pat. Nos. 4,874,554 and 4,137,180.

Use may be made of behenoylhydroxypropyltrimethylammonium chloride sold by KAO under the name Quatarmin BTC 131.

Preferably, the ammonium salts containing at least one ester function contain two ester functions.

Among the quaternary ammonium salts containing at least one ester function, which may be used, it is preferred to use dipalmitoyl-ethyl-hydroxy-ethyl-methyl-ammonium salts.

The cationic surfactants are preferably chosen from those of formula (V) and those of formula (VIII) and even more preferentially from those of formula (V).

The amphoteric or zwitterionic surfactant(s) that may be used in the composition according to the invention may especially be optionally quaternized secondary or tertiary aliphatic amine derivatives, in which the aliphatic group is a linear or branched chain comprising from 8 to 22 carbon atoms, said amine derivatives containing at least one anionic group, for instance a carboxylate, sulfonate, sulfate, phosphate or phosphonate group. Mention may be made in particular of ($C_8$-$C_{20}$alkyl)betaines, sulfobetaines, ($C_8$-$C_{20}$alkyl)amido($C_3$-$C_8$alkyl)betaines or ($C_8$-$C_{20}$alkyl)amido($C_6$-$C_8$-alkyl)sulfobetaines.

Among the optionally quaternized secondary or tertiary aliphatic amine derivatives that may be used, as defined above, mention may also be made of the compounds of respective structures (B1) and (B2) below:

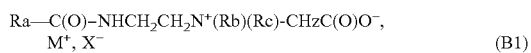

(B1)

in which formula (B1):
Ra represents a $C_{10}$-$C_{30}$ alkyl or alkenyl group derived from an acid RaCOOH, preferably present in hydrolysed coconut oil, or a heptyl, nonyl or undecyl group;
Rb represents a beta-hydroxyethyl group; and
Rc represents a carboxymethyl group;
$M^+$ represents a cationic counterion derived from an alkali metal or alkaline-earth metal, such as sodium, an ammonium ion or an ion derived from an organic amine; and
$X^-$ represents an organic or mineral anionic counterion, preferably chosen from halides, acetates, phosphates, nitrates, ($C_1$-$C_4$)alkyl sulfates, ($C_1$-$C_4$)alkyl or ($C_1$-$C_4$) alkylaryl sulfonates, in particular methyl sulfate and ethyl sulfate;
or alternatively $M^+$ and $X^-$ are absent;

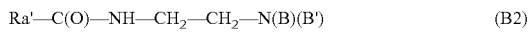

(B2)

in which formula:
B represents the group —$CH_2$—$CH_2$—O—X';
B' represents the group —($CH_2$)$_z$Y', with z=1 or 2;
X' represents the group —$CH_2$—C(O)OH, —$CH_2$—C(O)OZ', —$CH_2$—$CH_2$—C(O)OH, —$CH_2$—$CH_2$—C(O)OZ', or a hydrogen atom;
Y' represents the group —C(O)OH, —C(O)OZ', —$CH_2$—CH(OH)—$SO_3$H or the group —$CH_2$—CH(OH)—$SO_3$—Z';
Z' represents a cationic counterion derived from an alkali metal or alkaline-earth metal, such as sodium, an ammonium ion or an ion derived from an organic amine;
Ra' represents a $C_{10}$-$C_{30}$ alkyl or alkenyl group of an acid Ra'—COOH, which is preferably present in coconut oil or in hydrolysed linseed oil, or an alkyl group, especially a $C_{17}$ group and its iso form, or an unsaturated $C_{17}$ group.

The compounds of this type are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid and cocoamphodipropionic acid.

By way of example, mention may be made of the cocoamphodiacetate sold by the company Rhodia under the trade name Miranol® C2M Concentrate.

Use may also be made of the compounds of formula (B'2):

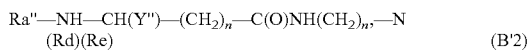

(B'2)

in which formula:
Y" represents the group —C(O)OH, —C(O)OZ", —$CH_2$—CH(OH)—$SO_3$H or the group —$CH_2$—CH(OH)—$SO_3$—Z";
Rd and Re, independently of each other, represent a $C_1$-$C_4$ alkyl or hydroxyalkyl radical;
Z" represents a cationic counterion derived from an alkali metal or alkaline-earth metal, such as sodium, an ammonium ion or an ion derived from an organic amine;
Ra" represents a $C_{10}$-$C_{30}$ alkyl or alkenyl group of an acid Ra"-C(O)OH which is preferably present in coconut oil or in hydrolysed linseed oil;
n and n' denote, independently of each other, an integer ranging from 1 to 3.

Among the compounds of formula (B'2), mention may be made of the compound classified in the CTFA dictionary under the name sodium diethylaminopropyl cocoaspartamide and sold by the company Chimex under the name Chimexane HB.

Among the abovementioned amphoteric or zwitterionic surfactants, it is preferred to use ($C_8$-$C_{20}$ alkyl)betaines such as cocoylbetaine, ($C_8$-$C_{20}$ alkyl)amido($C_2$-$C_5$ alkyl)betaines such as cocoylamidopropylbetaine, and mixtures thereof.

More preferentially, the amphoteric or zwitterionic surfactant(s) are chosen from cocoylamidopropylbetaine and cocoylbetaine.

Preferably, the composition according to the invention comprises one or more cationic surfactants, in particular such as those mentioned above.

Preferably, when they are present, the surfactant(s) represent a total content ranging from 0.1% to 20% by weight and better still from 0.5% to 10% by weight relative to the total weight of the composition.

Preferably, when they are present, the cationic surfactant(s) represent a total content ranging from 0.1% to 20% by weight, more preferentially from 0.5% to 10% by weight and better still from 1% to 5% by weight, relative to the total weight of the composition.

The composition according to the invention may also comprise one or more non-silicone fatty substances.

The term "fatty substance" means an organic compound that is insoluble in water at room temperature (25° C.) and at atmospheric pressure ($1.013 \times 10^5$ Pa) (solubility of less than 5% by weight, preferably less than 1% by weight and even more preferentially less than 0.1% by weight). They bear in their structure at least one hydrocarbon-based chain comprising at least 6 carbon atoms and/or a sequence of at least two siloxane groups. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane.

The term "non-silicone fatty substance" means a fatty substance whose structure does not comprise any silicon atoms, and which therefore especially does not comprise any siloxane groups. They generally bear in their structure a hydrocarbon-based chain comprising at least 6 carbon atoms. Advantageously, they are not oxyalkylenated and do not contain any —COOH functions.

The term "solid fatty substance" means a fatty substance that is solid at room temperature and atmospheric pressure (25° C., 1 atm); they preferably have a viscosity of greater than 2 Pa·s, measured at 25° C. and at a shear rate of 1 $s^{-1}$.

The non-silicone fatty substances, which are especially solid, that may be used in the context of the invention may be chosen from fatty alcohols, esters of a fatty acid and/or of a fatty alcohol, non-silicone waxes, ceramides, and mixtures thereof.

Preferably, the composition according to the invention comprises one or more fatty alcohols.

The term "fatty alcohol" means a long-chain aliphatic alcohol comprising from 8 to 40 carbon atoms and comprising at least one hydroxyl group OH. These fatty alcohols are neither oxyalkylenated nor glycerolated.

The solid fatty alcohols may be saturated or unsaturated, and linear or branched, and comprise from 8 to 40 carbon atoms. Preferably, the solid fatty alcohols have the structure R—OH with R denoting a linear alkyl group, optionally substituted with one or more hydroxyl groups, comprising from 8 to 40, better still from 10 to 30, or even from 12 to 24 atoms and even better still from 14 to 22 carbon atoms.

The solid fatty alcohols that may be used are preferably chosen from saturated or unsaturated, linear or branched, preferably linear and saturated, (mono)alcohols comprising from 8 to 40 carbon atoms, better still from 10 to 30, or even from 12 to 24 atoms and better still from 14 to 22 carbon atoms.

The solid fatty alcohols that may be used may be chosen, alone or as a mixture, from:
lauryl alcohol (or 1-dodecanol);
myristyl alcohol (or 1-tetradecanol);
cetyl alcohol (or 1-hexadecanol);
stearyl alcohol (or 1-octadecanol);
arachidyl alcohol (or 1-eicosanol);
behenyl alcohol (or 1-docosanol);
lignoceryl alcohol (or 1-tetracosanol);
ceryl alcohol (or 1-hexacosanol);
montanyl alcohol (or 1-octacosanol);
myricyl alcohol (or 1-triacontanol).

Preferentially, the solid fatty alcohol is chosen from cetyl alcohol, stearyl alcohol, behenyl alcohol, myristyl alcohol, and mixtures thereof, such as cetylstearyl alcohol or cetearyl alcohol.

The liquid fatty alcohols, in particular the $C_{10}$-$C_{34}$ alcohols, preferably have branched carbon-based chains or contain one or more, preferably 1 to 3, unsaturations. They are preferably branched and/or unsaturated, and comprise from 12 to 40 carbon atoms, and are non-oxyalkylenated and non-glycerolated.

Preferably, the liquid fatty alcohols are alcohols of structure R—OH as defined above with R denoting a branched saturated alkyl group. Preferably, R does not contain any hydroxyl groups. Mention may in particular be made of oleyl alcohol, linoleyl alcohol, linolenyl alcohol, isocetyl alcohol, isostearyl alcohol, 2-octyl-1-dodecanol, 2-butyloctanol, 2-hexyl-1-decanol, 2-decyl-1-tetradecanol and 2-tetradecyl-1-cetanol, and mixtures thereof.

Preferentially, the liquid fatty alcohol is 2-octyl-1-dodecanol.

Particularly preferably, the fatty alcohol(s) that may be used in the composition of the invention are chosen from cetyl alcohol, stearyl alcohol, behenyl alcohol, myristyl alcohol, cetylstearyl alcohol or cetearyl alcohol, and 2-octyl-1-dodecanol, and mixtures of these compounds.

The solid esters of a fatty acid and/or of a fatty alcohol that may be used are preferably chosen from esters derived from a $C_9$-$C_{26}$ carboxylic fatty acid and/or from a $C_9$-$C_{26}$ fatty alcohol.

Preferably, these solid fatty esters are esters of a linear or branched, saturated carboxylic acid comprising at least 10 carbon atoms, preferably from 10 to 30 carbon atoms and more particularly from 12 to 24 carbon atoms, and of a linear or branched, saturated monoalkyl, comprising at least 10 carbon atoms, preferably from 10 to 30 carbon atoms and more particularly from 12 to 24 carbon atoms. The saturated carboxylic acids may be optionally hydroxylated, and are preferably monocarboxylic acids.

Esters of $C_4$-$C_{22}$ dicarboxylic or tricarboxylic acids and of $C_1$-$C_{22}$ alcohols and esters of mono-, di- or tricarboxylic acids and of di-, tri-, tetra- or pentahydroxy alcohols which are $C_2$-$C_{26}$ may also be used.

Mention may in particular be made of octyldodecyl behenate, isocetyl behenate, cetyl lactate, stearyl octanoate, octyl octanoate, cetyl octanoate, decyl oleate, hexyl stearate, octyl stearate, myristyl stearate, cetyl stearate, stearyl stearate, octyl pelargonate, cetyl myristate, myristyl myristate, stearyl myristate, diethyl sebacate, diisopropyl sebacate, diisopropyl adipate, di-n-propyl adipate, dioctyl adipate, dioctyl maleate, octyl palmitate, myristyl palmitate, cetyl palmitate, stearyl palmitate, and mixtures thereof.

Preferably, the solid esters of a fatty acid and/or of a fatty alcohol are chosen from $C_9$-$C_{26}$ alkyl palmitates, especially myristyl, cetyl or stearyl palmitate; $C_9$-$C_{26}$ alkyl myristates, such as cetyl myristate, stearyl myristate and myristyl myristate; and $C_9$-$C_{26}$ alkyl stearates, especially myristyl stearate, cetyl stearate and stearyl stearate; and mixtures thereof.

For the purposes of the present invention, a wax is a lipophilic compound, which is solid at room temperature (25° C.) and atmospheric pressure, with a reversible solid/liquid change of state, having a melting point greater than about 40° C., which may be up to 200° C., and having in the solid state an anisotropic crystal organization. In general, the size of the wax crystals is such that the crystals diffract and/or scatter light, giving the composition that comprises them a more or less opaque cloudy appearance. By bringing the wax to its melting point, it is possible to make it miscible with oils and to form a microscopically homogeneous mixture, but on returning the temperature of the mixture to room temperature, recrystallization of the wax, which is microscopically and macroscopically detectable (opalescence), is obtained.

In particular, the waxes that are suitable for use in the invention may be chosen from waxes of animal, plant or mineral origin, non-silicone synthetic waxes, and mixtures thereof.

Mention may be made especially of hydrocarbon-based waxes, for instance beeswax, especially of biological origin, lanolin wax and Chinese insect waxes; rice bran wax, carnauba wax, candelilla wax, ouricury wax, alfalfa wax, berry wax, shellac wax, Japan wax and sumach wax; montan wax, orange wax, lemon wax, microcrystalline waxes, paraffins and ozokerite; polyethylene waxes, the waxes obtained by Fisher-Tropsch synthesis and waxy copolymers, and also esters thereof.

Mention may thus be made of $C_2$ to $C_{60}$ microcrystalline waxes, such as Microwax HW.

Mention may also be made of the PM 500 polyethylene wax sold under the reference Permalen 50-L polyethylene.

Mention may also be made of waxes obtained by catalytic hydrogenation of animal or plant oils containing linear or branched $C_8$ to $C_{32}$ fatty chains. Among these waxes mention may especially be made of isomerized jojoba oil such as the trans-isomerized partially hydrogenated jojoba oil, especially the product manufactured or sold by the company Desert Whale under the commercial reference Iso-Jojoba-50®, hydrogenated sunflower oil, hydrogenated castor oil, hydrogenated coconut oil, hydrogenated lanolin oil and bis(1,1,1-trimethylolpropane) tetrastearate, especially the product sold under the name Hest 2T-4S® by the company Heterene.

The waxes obtained by hydrogenation of castor oil esterified with cetyl alcohol, such as those sold under the names Phytowax Castor 16L64® and 22L73® by the company Sophim, may also be used.

A wax that may be also used is a $C_{20}$ to $C_{40}$ alkyl (hydroxystearyloxy)stearate (the alkyl group comprising from 20 to 40 carbon atoms), alone or as a mixture. Such a wax is especially sold under the names Kester Wax K 82 P®, Hydroxypolyester K 82 P® and Kester Wax K 80 P® by the company Koster Keunen.

It is also possible to use microwaxes in the compositions of the invention; mention may be made especially of carnauba microwaxes, such as the product sold under the name MicroCare 350® by the company Micro Powders, synthetic-wax microwaxes, such as the product sold under the name MicroEase 114S® by the company Micro Powders, microwaxes constituted of a mixture of carnauba wax and polyethylene wax, such as the products sold under the names Micro Care 300® and 310® by the company Micro Powders, microwaxes constituted of a mixture of carnauba wax and of synthetic wax, such as the product sold under the name Micro Care 325® by the company Micro Powders, polyethylene microwaxes, such as the products sold under the names Micropoly 200®, 220®, 220L® and 250S® by the company Micro Powders, and polytetrafluoroethylene microwaxes, such as the products sold under the names Microslip 519® and 519 L® by the company Micro Powders.

The waxes are preferably chosen from mineral waxes, for instance paraffin, petroleum jelly, lignite or ozokerite wax; plant waxes, for instance cocoa butter or cork fibre or sugar cane waxes, olive tree wax, rice wax, hydrogenated jojoba wax, ouricury wax, carnauba wax, candelilla wax, alfalfa wax, or absolute waxes of flowers, such as essential wax of blackcurrant flower sold by the company Bertin (France); waxes of animal origin, for instance beeswaxes or modified beeswaxes (cerabellina), spermaceti, lanolin wax and lanolin derivatives; microcrystalline waxes; and mixtures thereof.

The ceramides, or ceramide analogues such as glycoceramides, that may be used in the compositions according to the invention, are known; mention may in particular be made of ceramides of classes I, II, III and V according to the Dawning classification.

The ceramides or analogues thereof that may be used preferably correspond to the following formula:

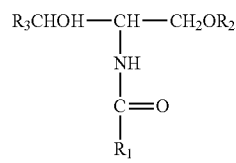

in which:
R₁ denotes a linear or branched, saturated or unsaturated alkyl group, derived from $C_{14}$-$C_{30}$ fatty acids, it being possible for this group to be substituted with a hydroxyl group in the alpha-position, or a hydroxyl group in the omega-position esterified with a saturated or unsaturated $C_{16}$-$C_{30}$ fatty acid;
R₂ denotes a hydrogen atom or a (glycosyl)n group, a (galactosyl)m group or a sulfogalactosyl group, in which n is an integer ranging from 1 to 4 and m is an integer ranging from 1 to 8;
R₃ denotes a $C_{15}$-$C_{26}$ hydrocarbon-based group, saturated or unsaturated in the alpha-position, it being possible for this group to be substituted with one or more $C_1$-$C_{14}$ alkyl groups;
it being understood that, in the case of natural ceramides or glycoceramides, R₃ may also denote a $C_{15}$-$C_{26}$ alpha-hydroxyalkyl group, the hydroxyl group being optionally esterified with a $C_{16}$-$C_{30}$ alpha-hydroxy acid.

The ceramides more particularly preferred are the compounds for which R₁ denotes a saturated or unsaturated alkyl derived from $C_{16}$-$C_{22}$ fatty acids; R₂ denotes a hydrogen atom and R₃ denotes a linear, saturated $C_{15}$ group.

Preferentially, use is made of ceramides for which $R_1$ denotes a saturated or unsaturated alkyl group derived from $C_{14}$-$C_{30}$ fatty acids; $R_2$ denotes a galactosyl or sulfogalactosyl group; and $R_3$ denotes a —CH═CH—(CH$_2$)$_{12}$—CH$_3$ group.

Use may also be made of the compounds for which $R_1$ denotes a saturated or unsaturated alkyl radical derived from $C_{12}$-$C_{22}$ fatty acids; $R_2$ denotes a galactosyl or sulfogalactosyl radical; and $R_3$ denotes a saturated or unsaturated $C_{12}$-$C_{22}$ hydrocarbon-based radical and preferably a —CH═CH—(CH$_2$)$_{12}$—CH$_3$ group.

As compounds that are particularly preferred, mention may also be made of 2-N-linoleoylaminooctadecane-1,3-diol; 2-N-oleoylaminooctadecane-1,3-diol; 2-N-palmitoylaminooctadecane-1,3-diol; 2-N-stearoylaminooctadecane-1,3-diol; 2-N-behenoylaminooctadecane-1,3-diol; 2-N-[2-hydroxypalmitoyl]aminooctadecane-1,3-diol; 2-N-stearoylaminooctadecane-1,3,4 triol and in particular N-stearoylphytosphingosine; 2-N-palmitoylaminohexadecane-1,3-diol, N-linoleoyldihydrosphingosine, N-oleoyldihydrosphingosine, N-palmitoyldihydrosphingosine, N-stearoyldihydrosphingosine, and N-behenoyldihydrosphingosine, N-docosanoyl-N-methyl-D-glucamine, cetylic acid N-(2-hydroxyethyl)-N-(3-cetyloxy-2-hydroxypropyl)amide and bis(N-hydroxyethyl-N-cetyl)malonamide; and mixtures thereof. N-oleoyldihydrosphingosine will preferably be used.

Preferably, the composition according to the invention comprises one or more fatty alcohols, which are preferably solid.

When they are present, the fatty substance(s) generally represent a total content ranging from 0.1% to 15% by weight, preferably from 1% to 10% by weight and more preferentially from 2% to 8% by weight, relative to the total weight of the composition.

The pH of the composition according to the invention generally ranges from 2 to 8, preferably from 2.5 to 6 and better still from 3 to 5.5.

The pH of the composition of the invention may be adjusted and/or stabilized by means of basifying agents and acidifying agents that are well known to those skilled in the art.

Basifying agents that may especially be mentioned include aqueous ammonia, alkali metal carbonates or bicarbonates, organic amines with a pKb at 25° C. of less than 12, in particular less than 10 and even more advantageously less than 6; among the salts of the amines mentioned previously with acids such as carbonic acid or hydrochloric acid, it should be noted that it is the pKb corresponding to the function of highest basicity.

Preferably, the amines are chosen from alkanolamines, in particular comprising a primary, secondary or tertiary amine function, and one or more linear or branched $C_1$-$C_8$ alkyl groups bearing one or more hydroxyl radicals; from oxyethylenated and/or oxypropylenated ethylenediamines, and from amino acids and compounds having the following formula:

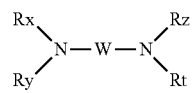

in which W is a $C_1$-$C_6$ alkylene residue optionally substituted with a hydroxyl group or a $C_1$-$C_6$ alkyl radical; Rx, Ry, Rz and Rt, which may be identical or different, represent a hydrogen atom or a $C_1$-$C_6$ alkyl, $C_1$-$C_6$ hydroxyalkyl or $C_1$-$C_6$ aminoalkyl radical.

Acidifying agents that may especially be mentioned include hydrochloric acid, (ortho)phosphoric acid, sulfuric acid, boric acid, and also carboxylic acids, for instance acetic acid, lactic acid or citric acid, or sulfonic acids.

The composition according to the invention may comprise one or more silicones.

The silicones that may be present in the composition according to the invention may be solid or liquid, volatile or non-volatile, and amino or non-amino. The composition may, of course, comprise a mixture of such silicones.

As silicones that may be used, mention may be made, alone or as a mixture, of polydialkylsiloxanes and especially polydimethylsiloxanes (PDMSs), polydiarylsiloxanes, polyalkylarylsiloxanes, silicone gums and resins, and also organopolysiloxanes (or organomodified polysiloxanes, or alternatively organomodified silicones) which are polysiloxanes comprising in their structure one or more organofunctional groups, generally attached via a hydrocarbon-based group, and preferably chosen from aryl groups, amino groups, alkoxy groups and polyoxyethylene or polyoxypropylene groups.

The organomodified silicones may be polydiarylsiloxanes, in particular polydiphenylsiloxanes, and polyalkylarylsiloxanes, functionalized with the organofunctional groups mentioned previously. The polyalkylarylsiloxanes are particularly chosen from linear and/or branched polydimethyl/methylphenylsiloxanes and polydimethyl/diphenylsiloxanes.

Among the organomodified silicones, mention may be made of organopolysiloxanes comprising:

polyoxyethylene and/or polyoxypropylene groups optionally comprising $C_6$-$C_{24}$ alkyl groups, such as dimethicone copolyols and especially those sold by the company Dow Corning under the name DC 1248 or the oils Silwet® L 722, L 7500, L 77 and L 711 from the company Union Carbide; or ($C_{12}$)alkylmethicone copolyols and especially those sold by the company Dow Corning under the name Q2 5200;

substituted or unsubstituted amine groups, in particular $C_1$-$C_4$ aminoalkyl groups; mention may be made of the products sold under the names GP4 Silicone Fluid and GP7100 by the company Genesee, or under the names Q2-8220 and DC929 or DC939 by the company Dow Corning;

thiol groups, such as the products sold under the names GP 72 A and GP 71 from Genesee;

alkoxy groups such as the product sold under the name Silicone Copolymer F-755 by SWS Silicones, and Abil Wax® 2428, 2434 and 2440 by the company Goldschmidt;

hydroxylated groups, for instance polyorganosiloxanes bearing a hydroxyalkyl function;

acyloxyalkyl groups, such as the polyorganosiloxanes described in patent U.S. Pat. No. 4,957,732;

anionic groups of the carboxylic acid type, as described, for example, in EP 186 507, or of the alkylcarboxylic type, such as the product X-22-3701E from the company Shin-Etsu; or alternatively of the 2-hydroxyalkylsulfonate or 2-hydroxyalkylthiosulfate type, such as the products sold by the company Goldschmidt under the names Abil® S201 and Abil® S255;

hydroxyacylamino groups, such as the polyorganosiloxanes described in patent application EP 342 834;

mention may be made, for example, of the product Q2-8413 from the company Dow Corning.

The silicones may also be chosen from polydialkylsiloxanes, among which mention may be made mainly of polydimethylsiloxanes bearing trimethylsilyl end groups. Among these polydialkylsiloxanes, mention may be made of the following commercial products:

the Silbione® oils of the 47 and 70 047 series or the Mirasil® oils sold by Rhodia, for instance the oil 70 047 V 500 000;

the oils of the Mirasil® series sold by the company Rhodia;

the oils of the 200 series from the company Dow Corning, such as DC200 with a viscosity of 60 000 mm²/s;

the Viscasil® oils from General Electric and certain oils of the SF series (SF 96, SF 18) from General Electric.

Mention may also be made of polydimethylsiloxanes bearing dimethylsilanol end groups, known under the name dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are polydi($C_1$-$C_{20}$)alkylsiloxanes.

Products that may be used more particularly in accordance with the invention are mixtures such as:

mixtures formed from a polydimethylsiloxane with a hydroxy-terminated chain, or dimethiconol (CTFA), and from a cyclic polydimethylsiloxane, also known as cyclomethicone (CTFA), such as the product Q2-1401 sold by the company Dow Corning.

The polyalkylarylsiloxanes are particularly chosen from linear and/or branched polydimethyl/methylphenylsiloxanes and polydimethyl/diphenylsiloxanes with a viscosity ranging from $1 \times 10^{-5}$ to $5 \times 10^{-2}$ m²/s at 25° C.

Among these polyalkylarylsiloxanes, mention may be made of the products sold under the following names:

the Silbione® oils of the 70 641 series from Rhodia;

the oils of the Rhodorsil® 70 633 and 763 series from Rhodia;

the oil Dow Corning 556 Cosmetic Grade Fluid from Dow Corning;

the silicones of the PK series from Bayer, such as the product PK20;

the silicones of the PN and PH series from Bayer, such as the products PN1000 and PH1000;

certain oils of the SF series from General Electric, such as SF 1023, SF 1154, SF 1250 and SF 1265.

According to one variant of the invention, when the composition comprises one or more silicones, the composition preferably comprises one or more amino silicones. The term "amino silicone" denotes any silicone comprising at least one primary, secondary or tertiary amine or a quaternary ammonium group.

The weight-average molecular masses of these amino silicones may be measured by gel permeation chromatography (GPC) at room temperature (25° C.), as polystyrene equivalent. The columns used are µ styragel columns. The eluent is THF and the flow rate is 1 ml/min. 200 µl of a 0.5% by weight solution of silicone in THF are injected. Detection is performed by refractometry and UV-metry.

As amino silicone that may be used in the context of the invention, mention may be made of:

a) the polysiloxanes corresponding to formula (A):

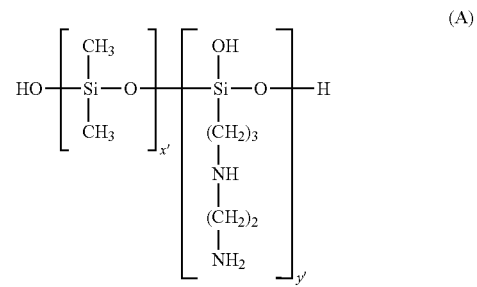

(A)

in which x' and y' are integers such that the weight-average molecular weight (Mw) is between 5000 and 500 000 approximately;

b) the amino silicones corresponding to formula (B):

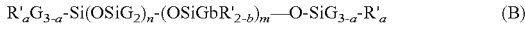

(B)

in which:

G, which may be identical or different, denotes a hydrogen atom or a phenyl, OH or $C_1$-$C_8$ alkyl, for example methyl, or $C_1$-$C_8$ alkoxy, for example methoxy, group, a, which may be identical or different, denotes 0 or an integer from 1 to 3, in particular 0, b denotes 0 or 1, in particular 1, m and n are numbers such that the sum (n+m) ranges from 1 to 2000 and in particular from 50 to 150, n possibly denoting a number from 0 to 1999 and in particular from 49 to 149, and m possibly denoting a number from 1 to 2000 and in particular from 1 to 10;

R', which may be identical or different, denotes a monovalent radical of formula —$C_qH_{2q}$L in which q is a number ranging from 2 to 8 and L is an optionally quaternized amino group chosen from the following groups:

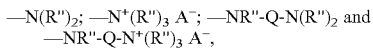

in which R'', which may be identical or different, denotes hydrogen, phenyl, benzyl, or a saturated monovalent hydrocarbon-based radical, for example a $C_1$-$C_{20}$ alkyl radical; Q denotes a linear or branched group of formula $C_rH_{2r}$, r being an integer ranging from 2 to 6, preferably from 2 to 4; and A⁻ represents a cosmetically acceptable anion, in particular a halide such as fluoride, chloride, bromide or iodide anion.

A first group of amino silicones corresponding to formula (B) is represented by the silicones known as "trimethylsilyl amodimethicone", corresponding to formula (C):

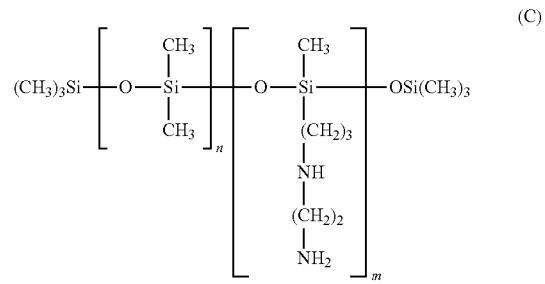

(C)

in which m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10.

A second group of amino silicones corresponding to formula (B) is represented by the silicones of formula (D) below:

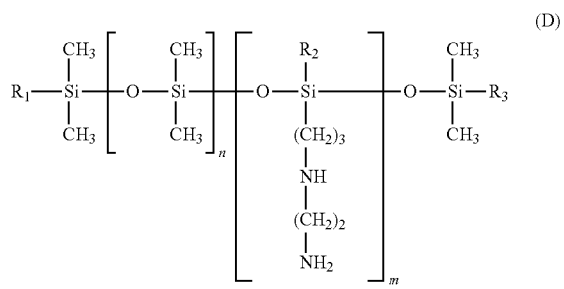

(D)

in which:

m and n are numbers such that the sum (n+m) ranges from 1 to 1000 and in particular from 50 to 250 and more particularly from 100 to 200; it being possible for n to denote a number from 0 to 999 and in particular from 49 to 249 and more particularly from 125 to 175, and for m to denote a number from 1 to 1000 and in particular from 1 to 10, and more particularly from 1 to 5;

$R_1$, $R_2$ and $R_3$, which may be identical or different, represent a hydroxyl or $C_1$-$C_4$ alkoxy radical, at least one of the radicals $R_1$ to $R_3$ denoting an alkoxy radical.

Preferably, the alkoxy radical is a methoxy radical.

The hydroxy/alkoxy mole ratio ranges preferably from 0.2:1 to 0.4:1 and preferably from 0.25:1 to 0.35:1 and more particularly equals 0.3:1.

The weight-average molecular mass (Mw) of these silicones preferably ranges from 2000 to 1 000 000 and more particularly from 3500 to 200 000.

A third group of amino silicones corresponding to formula (B) is represented by the silicones of formula (E) below:

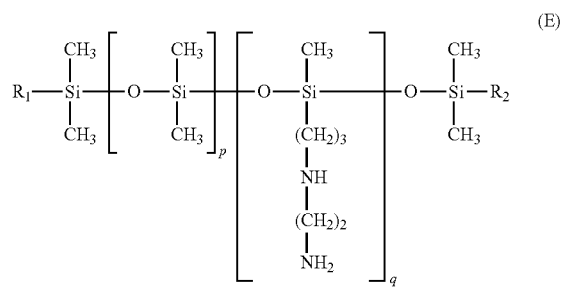

(E)

in which:

p and q are numbers such that the sum (p+q) ranges from 1 to 1000, in particular from 50 to 350 and more particularly from 150 to 250; it being possible for p to denote a number from 0 to 999 and in particular from 49 to 349 and more particularly from 159 to 239, and for q to denote a number from 1 to 1000, in particular from 1 to 10 and more particularly from 1 to 5;

$R_1$ and $R_2$, which are different, represent a hydroxyl or $C_1$-$C_4$ alkoxy radical, at least one of the radicals $R_1$ or $R_2$ denoting an alkoxy radical.

Preferably, the alkoxy radical is a methoxy radical.

The hydroxy/alkoxy mole ratio generally ranges from 1:0.8 to 1:1.1 and preferably from 1:0.9 to 1:1 and more particularly equals 1:0.95.

The weight-average molecular mass (Mw) of the silicone preferably ranges from 2000 to 200 000, even more particularly from 5000 to 100 000 and more particularly from 10 000 to 50 000.

The commercial products comprising silicones of structure (D) or (E) may include in their composition one or more other amino silicones of which the structure is different from formula (D) or (E).

A product containing amino silicones of structure (D) is sold by the company Wacker under the name Belsil® ADM 652.

A product containing amino silicones of structure (E) is sold by Wacker under the name Fluid WR 1300® or Belsil® ADM LOG 1.

When these amino silicones are used, one particularly advantageous embodiment consists in using them in the form of an oil-in-water emulsion. The oil-in-water emulsion may comprise one or more surfactants. The surfactants may be of any nature but are preferably cationic and/or nonionic. The numerical mean size of the silicone particles in the emulsion generally ranges from 3 nm to 500 nm. Preferably, in particular as amino silicones of formula (E), use is made of microemulsions of which the mean particle size ranges from 5 nm to 60 nm (limits included) and more particularly from 10 nm to 50 nm (limits included). Thus, use may be made according to the invention of the amino silicone microemulsions of formula (E) sold under the names Finish CT 96 E® or SLM 28020® by the company Wacker.

Another group of amino silicones corresponding to formula (B) is represented by the silicones of formula (F) below:

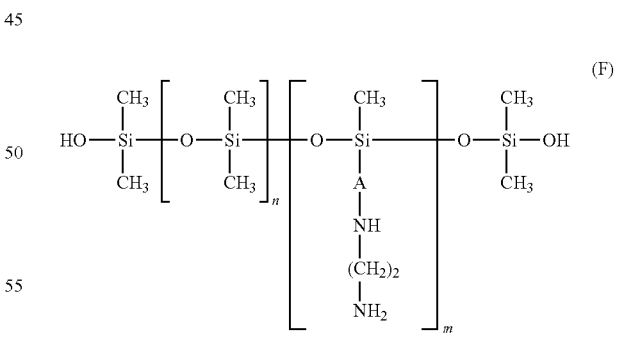

(F)

in which:

m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;

A denotes a linear or branched alkylene radical containing from 4 to 8 carbon atoms and preferably 4 carbon atoms. This radical is preferably linear.

The weight-average molecular mass (Mw) of these amino silicones preferably ranges from 2000 to 1 000 000 and even more particularly from 3500 to 200 000.

A silicone corresponding to this formula is, for example, the Xiameter MEM 8299 Emulsion from Dow Corning.

Another group of amino silicones corresponding to formula (B) is represented by the silicones of formula (G) below:

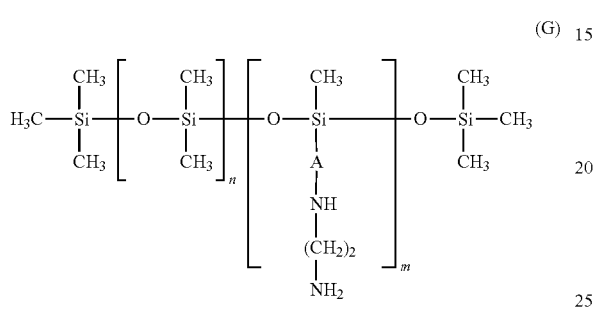
(G)

in which:
m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;

A denotes a linear or branched alkylene radical containing from 4 to 8 carbon atoms and preferably 4 carbon atoms, This radical is preferably branched.

The weight-average molecular mass (Mw) of these amino silicones preferably ranges from 500 to 1 000 000 and even more particularly from 1000 to 200 000.

A silicone corresponding to this formula is, for example, DC2-8566 Amino Fluid from Dow Corning.

c) the amino silicones corresponding to formula (H):

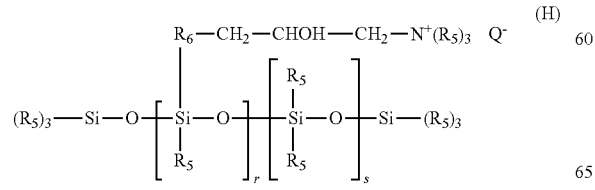
(H)

in which:

$R_5$ represents a monovalent hydrocarbon-based radical containing from 1 to 18 carbon atoms, and in particular a $C_1$-$C_{18}$ alkyl or $C_2$-$C_{18}$ alkenyl, for example methyl, radical;

$R_6$ represents a divalent hydrocarbon-based radical, in particular a $C_1$-$C_{18}$ alkylene radical or a divalent $C_1$-$C_{18}$, for example $C_1$-$C_8$, alkyleneoxy radical linked to the Si via an SiC bond;

$Q^-$ is an anion such as a halide, especially chloride, ion or an organic acid salt, especially acetate;

r represents a mean statistical value ranging from 2 to 20 and in particular from 2 to 8;

s represents a mean statistical value ranging from 20 to 200 and in particular from 20 to 50.

Such amino silicones are in particular described in patent U.S. Pat. No. 4,185,087.

d) the quaternary ammonium silicones of formula (I'):

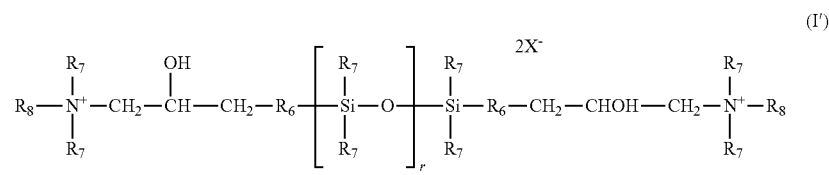
(I')

in which:

$R_7$, which may be identical or different, represent a monovalent hydrocarbon-based radical containing from 1 to 18 carbon atoms, and in particular a $C_1$-$C_{18}$ alkyl radical, a $C_2$-$C_{18}$ alkenyl radical or a ring comprising 5 or 6 carbon atoms, for example a methyl radical;

$R_6$ represents a divalent hydrocarbon-based radical, in particular a $C_1$-$C_{18}$ alkylene radical or a divalent $C_1$-$C_{18}$, for example $C_1$-$C_8$, alkyleneoxy radical linked to the Si via an SiC bond;

$R_8$, which may be identical or different, represent a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a radical —$R_6$—$NHCOR_7$;

$X^-$ is an anion such as a halide, especially chloride, ion or an organic acid salt, especially acetate;

r represents a mean statistical value ranging from 2 to 200 and in particular from 5 to 100.

These silicones are described, for example, in patent application EP-A 0 530 974.

e) the amino silicones of formula (J):

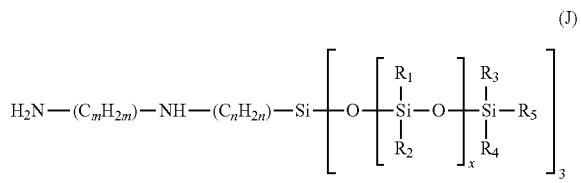

in which:
- $R_1$, $R_2$, $R_3$ and $R_4$, which may be identical or different, denote a $C_1$-$C_4$ alkyl radical or a phenyl group,
- $R_5$ denotes a $C_1$-$C_4$ alkyl radical or a hydroxyl group,
- n is an integer ranging from 1 to 5,
- m is an integer ranging from 1 to 5, and
- x is chosen such that the amine number ranges from 0.01 to 1 meq/g.

f) multiblock polyoxyalkylenated amino silicones, of the type $(AB)_n$, A being a polysiloxane block and B being a polyoxyalkylene block comprising at least one amine group.

Said silicones preferably are constituted of repeating units of the following general formulae:

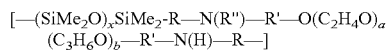

or alternatively

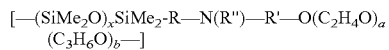

in which:
- a is an integer greater than or equal to 1, preferably ranging from 5 to 200 and more particularly ranging from 10 to 100;
- b is an integer between 0 and 200, preferably ranging from 4 to 100 and more particularly between 5 and 30;
- x is an integer ranging from 1 to 10 000 and more particularly from 10 to 5000;
- R" is a hydrogen atom or a methyl;
- R, which may be identical or different, represent a linear or branched divalent $C_2$-$C_{12}$ hydrocarbon-based radical, optionally comprising one or more heteroatoms such as oxygen; preferably, R denotes an ethylene radical, a linear or branched propylene radical, a linear or branched butylene radical or a radical —$CH_2CH_2CH_2OCH(OH)CH_2$—; preferentially, R denotes a radical —$CH_2CH_2CH_2OCH(OH)CH_2$—;
- R', which may be identical or different, represent a linear or branched divalent $C_2$-$C_{12}$ hydrocarbon-based radical, optionally comprising one or more heteroatoms such as oxygen; preferably, R' denotes an ethylene radical, a linear or branched propylene radical, a linear or branched butylene radical or a radical —$CH_2CH_2CH_2OCH(OH)CH_2$—; preferentially, R' denotes —$CH(CH_3)$—$CH_2$—.

The siloxane blocks preferably represent from 50 mol % to 95 mol % of the total weight of the silicone, more particularly from 70 mol % to 85 mol %.

The amine content is preferably between 0.02 and 0.5 meq/g of copolymer in a 30% solution in dipropylene glycol, more particularly between 0.05 and 0.2.

The weight-average molecular mass (Mw) of the silicone is preferably between 5000 and 1 000 000 and more particularly between 10 000 and 200 000.

Mention may be made especially of the silicones sold under the names Silsoft A-843 or Silsoft A+ by Momentive.

The composition preferably comprises one or more silicones corresponding to formula (B), preferably to one of formulae (C), (D), (E), (F) and (G), and most particularly corresponding to formula (E) or (F).

When the composition according to the invention comprises said silicone(s), they are preferably included in a total amount ranging from 0.1% to 5% by weight, preferentially from 0.2% to 2.5% by weight and better still from 0.3% to 1% by weight, relative to the total weight of the composition.

The composition according to the invention may also contain additives such as natural or synthetic, anionic, amphoteric or zwitterionic, nonionic or cationic, associative or non-associative polymeric thickeners, non-polymeric thickeners such as electrolytes, styling polymers, sugars, nacreous agents, opacifiers, sunscreens, vitamins or provitamins, fragrances and organic or mineral particles.

A person skilled in the art will take care to select the optional additives and the amount thereof such that they do not harm the properties of the compositions of the present invention.

These additives are generally present in the composition according to the invention in an amount ranging from 0 to 20% by weight relative to the total weight of the composition.

The present invention also relates to a process for cosmetic treatment of keratin fibres using said composition.

This process consists in applying the composition according to the invention to dry or wet keratin fibres, that have optionally been washed with a shampoo. Preferably, the composition according to the invention is applied to wet keratin fibres.

After an optional leave-on time, the keratin fibres are optionally rinsed with water, optionally washed with a shampoo and then rinsed with water, before being dried or left to dry.

The composition according to the present invention is generally applied with a leave-on time that may range from 1 to 15 minutes, preferably from 2 to 10 minutes.

Finally, the present invention relates to the use of the cosmetic composition as defined previously for treating keratin fibres, preferably human keratin fibres such as the hair.

The examples that follow serve to illustrate the invention without, however, being limiting in nature.

EXAMPLES

Measuring Method

The efficacy of the preserving agent according to the invention is evaluated by means of the Challenge test, which makes it possible to determine the level of antimicrobial protection of a composition.

It consists of artificial contamination of the test product with various microorganisms (bacteria, yeasts and moulds) and monitoring of the number of germs that are viable over time.

This is why, before the start of the test, a cleanliness control must be performed. This makes it possible to check that the formulations that are to be tested in the Challenge test are not contaminated or that they meet the tolerated standards. Thus, multiple contaminations are avoided for correct progress of the Challenge test.

A product that is satisfactorily protected must enable decontamination of the microorganisms introduced, this decontamination being more or less rapid as a function of the microbial strains, the type of product, the conditioning article, etc.

Artificial contamination with various organisms, or inoculation, proceeds in an identical manner for the two steps: 1) orientation and 2) confirmation.

The product is distributed in as many pill bottles as there are microorganisms to be tested. A calibrated microorganism suspension is introduced into each of these bottles so as to obtain a content of 106 germs per gram of product (each microorganism suspension is counted to determine the exact content inoculated in the product).

The contaminated product is stored at 22±2° C.

The efficacy of protection of the formulations is tested on a microbial spectrum that is limited but chosen from among species that are liable to contaminate the product both during manufacture and during its use.

The microbial spectrum combines the various microorganisms used to perform a Challenge test. It comprises four bacteria (*Escherichia coli, Pseudomonas aeruginosa, Staphylococcus aureus* and *Enterococcus faecalis*), one yeast (*Candida albicans*) and one mould (*Aspergillus niger*).

1st Part of the Test: Orientation

This is a screening test for orienting the rest of the tests and for identifying in a short space of time the formulations that are insufficiently protected.

After 7 days of contact between the product and the germ, a sample is taken for the purpose of counting the microorganisms remaining in the product.

Detection limit via this method: 200 cfu/g

The most favourable result is thus less than 200 germs/g (absence of microbial colonies on the dishes).

2nd Part of the Test: Confirmation

Excluding special cases, only the formulations retained on conclusion of the orientation test can undergo the confirmation step.

As for the orientation, the first sample collection for counting of the microorganisms remaining in the product takes place after 7 days of contact between the product and the germ.

The major difference between the confirmation step and the orientation step is that two other sample collections will be performed so as to monitor the change in antimicrobial protection over time: a sample collection at 14 days and another at 28 days.

The dilutions made to perform the counting are seeded in Petri dishes.

The germs remaining in the product are counted.

Example: $4.3 \times 10^5$ germs/g

Detection limit of this method: 200 cfu/g The most favourable result is thus less than 200 germs/g (absence of microbial colonies on the Petri dishes).

In order to check the stability of the antimicrobial protection over time, this test is repeated on the formulation after 2 months of accelerated ageing at 45° C.

Composition a (g % of AM)

| Ingredient | Content |
| --- | --- |
| Hydroxyethylcellulose (MW: 1 300 000) | 0.25 |
| Cetearyl alcohol | 0.7 |
| Cetyl alcohol | 3.7 |
| Mixture of myristyl stearate and myristyl palmitate | 0.8% AM |
| Myristyl alcohol | 0.4 |
| Dipalmitoylethylhydroxyethylmethylammonium methosulfate | 0.3% AM |
| Cetrimonium chloride | 0.63% AM |
| Behentrimonium chloride | 0.47% AM |
| Polydimethylsiloxane bearing aminoethyl iminopropyl groups | 0.55% AM |
| pH agents | qs pH = 3.5 ± 0.5 |
| Preserving agent | X % |
| Water | qs 100 |

The following preserving agents were introduced into the haircare composition A described above at the concentrations respectively indicated (in g %), leading to compositions B, C and D.

| Ingredient | B (comp.) | C (inv.) | D (inv.) | E (comp.) |
| --- | --- | --- | --- | --- |
| 4-(3-Ethoxy-4-hydroxyphenyl)-2-butanone (compound of formula (I)) | 0.01 | 0.01 | 0.01 | — |
| Salicylic acid | — | 0.02 | 0.02 | 0.02 |
| 1,3-Propanediol | 0.1 | — | 0.1 | 0.1 |

Comparative compositions B and E and compositions C and D according to the invention were subjected to the Challenge test according to the protocol described previously.

Results:

The results of the confirmation step on conclusion of 2 months of accelerated ageing at 45° C. are presented below.

| Tests | B | C | D | E |
| --- | --- | --- | --- | --- |
| Confirmation (2 months at 45° C.) | * | ** | ** | — |

These results show that the preserving agents according to the invention, present in compositions C and D, ensure satisfactory microbial protection, better than that obtained with 4-(3-ethoxy-4-hydroxyphenyl)-2-butanone alone but present in small amount (composition B) and markedly better than that obtained with the combination of salicylic acid and propanediol (composition E) which affords unsatisfactory conservation.

The invention claimed is:

1. A synergistic preserving agent for protecting a hair cosmetic composition against contamination from a microorganism comprising:
a first compound of formula (I) below, present in a content ranging from 0.005% to 0.1% by weight relative to the total weight of the hair cosmetic composition containing the preserving agent:

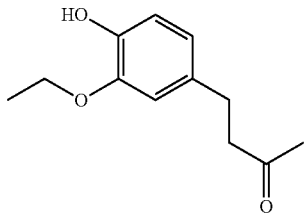

at least one diol comprising from 2 to 6 carbon atoms, present in a content ranging from 0.01% to 1% by weight relative to the total weight of the hair cosmetic composition containing the preserving agent, and wherein the weight ratio of the first compound to the at least one diol ranges from 0.01 to 1, and at least salicylic acid, present in a content ranging from 0.01% to 0.05% by weight relative to the total weight of the hair cosmetic composition containing the preserving agent;

wherein the first compound of formula (I) and the salicylic acid show a synergistic antimicrobial effect.

2. The preserving agent according to claim 1, wherein the weight ratio of the first compound to the at least salicylic acid ranges from 0.01 to 10.

3. The preserving agent according to claim 1, wherein the at least one diol comprises from 2 to 4 carbon atoms.

4. The preserving agent according to claim 3, characterized in that the diol(s) are chosen from 1,2-propanediol, 1,3-propanediol, and a mixture of these compounds.

5. The preserving agent according to claim 3, wherein the weight ratio of the first compound to the at least salicylic acid ranges from 0.01 to 10.

6. The preserving agent according to claim 4, wherein the weight ratio of the first compound to the at least salicylic acid ranges from 0.01 to 10.

7. A preserving agent for protecting a hair cosmetic composition against contamination from a microorganism comprising:

a first compound of formula (I) below, present in a content ranging from 0.005% to 0.01% by weight relative to the total weight of the hair cosmetic composition containing the preserving agent:

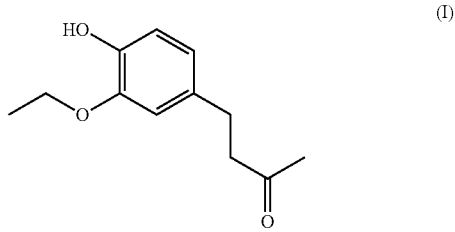

at least one diol comprising from 2 to 6 carbon atoms, present in a content ranging from 0.01% to 1% by weight relative to the total weight of the hair cosmetic composition containing the preserving agent, and wherein the weight ratio of the first compound to the at least one diol ranges from 0.01 to 1, and at least salicylic acid, present in a content ranging from 0.01% to 0.05% by weight relative to the total weight of the hair cosmetic composition containing the preserving agent.

* * * * *